United States Patent
Masoud et al.

(10) Patent No.: US 7,742,816 B2
(45) Date of Patent: Jun. 22, 2010

(54) MULTICHANNEL COMMUNICATION FOR IMPLANTABLE MEDICAL DEVICE APPLICATIONS

(75) Inventors: Javaid Masoud, Shoreview, MN (US); Christopher C. Fuller, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 161 days.

(21) Appl. No.: 11/278,176

(22) Filed: Mar. 31, 2006

(65) Prior Publication Data

US 2007/0239229 A1  Oct. 11, 2007

(51) Int. Cl.
*A61N 1/00* (2006.01)

(52) U.S. Cl. .......................... 607/32; 607/60

(58) Field of Classification Search ............. 607/30–32, 607/59, 60
See application file for complete search history.

(56) References Cited

U.S. PATENT DOCUMENTS

| | | | |
|---|---|---|---|
| 4,401,119 A | 8/1983 | Herpers | |
| 4,886,064 A | 12/1989 | Strandberg | |
| 4,987,897 A | 1/1991 | Funke | |
| 5,113,859 A | 5/1992 | Funke | |
| 5,331,966 A | 7/1994 | Bennett | |
| 5,345,362 A | 9/1994 | Winkler | |
| 5,350,411 A | 9/1994 | Ryan et al. | |
| 5,564,434 A | 10/1996 | Halperin et al. | |
| 5,626,620 A | 5/1997 | Kieval et al. | |
| 5,683,432 A | 11/1997 | Goedeke et al. | |
| 5,931,857 A | 8/1999 | Prieve et al. | |
| 6,236,889 B1 | 5/2001 | Soykan et al. | |
| 6,441,747 B1 | 8/2002 | Khair et al. | |
| 6,473,638 B2 | 10/2002 | Ferek-Petric | |
| 6,516,227 B1 | 2/2003 | Meadows et al. | |
| 6,668,196 B1 | 12/2003 | Villegas et al. | |
| 6,842,647 B1 | 1/2005 | Griffith et al. | |
| 6,878,112 B2 | 4/2005 | Linberg et al. | |
| 7,013,178 B2* | 3/2006 | Reinke et al. | 607/60 |
| 2002/0026224 A1 | 2/2002 | Thompson et al. | |
| 2003/0083714 A1 | 5/2003 | Thompson et al. | |
| 2003/0220673 A1 | 11/2003 | Snell | |
| 2005/0113885 A1 | 5/2005 | Haubrich et al. | |
| 2005/0197680 A1 | 9/2005 | DelMain et al. | |
| 2005/0251228 A1* | 11/2005 | Hamel | 607/60 |
| 2006/0161222 A1 | 7/2006 | Haubrich et al. | |
| 2007/0032830 A1* | 2/2007 | Bowers | 607/5 |

OTHER PUBLICATIONS

International Search Report for International Patent Application No. PCT/US2007/063600, mailed Oct. 10, 2007.

* cited by examiner

*Primary Examiner*—Scott M Getzow

(57) ABSTRACT

An implantable medical device ("IMD") as described herein is configured to support concurrent multichannel data communication with one or more other devices within a body area network corresponding to a patient. The IMD, and possibly other devices within the body area network, can support the multichannel communication with any number of additional IMDs implanted within the body of the same patient. Moreover, one or more of the concurrent data communication channels may be a full-duplex channel. Example embodiments can be flexibly configured to support different data communication protocols and/or different modulation schemes as needed to suit the particular application or operating environment.

16 Claims, 7 Drawing Sheets

MULTICHANNEL COMMUNICATION FOR IMPLANTABLE MEDICAL DEVICE APPLICATIONS

TECHNICAL FIELD

The present invention relates generally to implantable medical devices. More particularly, the present invention relates to telemetry communications involving such implanted medical devices.

BACKGROUND

Implantable medical devices ("IMDs") are used to provide therapies to patients suffering from a variety of conditions. Examples of IMDs involving cardiac devices are implantable pacemakers and implantable cardioverter-defibrillators ("ICDs"). Such electronic medical devices generally monitor the electrical activity of the heart and provide electrical stimulation to one or more of the heart chambers as needed. For example, pacemakers are designed to sense arrhythmias, i.e., disturbances in heart rhythm, and, in turn, provide appropriate electrical stimulation pulses at a controlled rate to selected chambers of the heart in order to correct the arrhythmias and restore the proper heart rhythm. The types of arrhythmias that may be detected and corrected by IMDs include bradycardias (unusually slow heart rates) and certain tachycardias (unusually fast heart rates).

ICDs also detect arrhythmias and provide appropriate electrical stimulation pulses to selected chambers of the heart to correct abnormal heart rate. In contrast to pacemakers, however, an ICD can also provide pulses that are much stronger and less frequent, where such pulses are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy therapy pulses to the heart.

Generally, IMDs are equipped with on-board memory in which telemetered signals can be stored for later retrieval and analysis. Typically, the telemetered signals can provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, IMDs store the telemetered signals over a set period of time (usually before, during, and after the occurrence of such arrhythmic event). Current practice in the art involves the use of an external communication unit, e.g., an external programmer, for non-invasive communication with IMDs via uplink and downlink communication channels associated with the communication device. In accordance with conventional medical device programming systems, a programming head can be used for facilitating two-way half duplex communication between IMDs and the external communication device. In many known IMD systems, the programming head can be positioned on the patient's body over the IMD such that the programming head can send wireless signals to, and receive wireless signals from, the IMD in accordance with common practice in the art.

Implementation and operation of most, if not all, RF communication systems for IMDs and external communication devices involves a balancing or compromising of certain countervailing considerations, relating to such interrelated operational parameters as data transmission rate and transmission range, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. For example, conventional IMD systems are limited in that they typically employ half-duplex data communication techniques over a single communication channel. Although some existing IMDs can communicate with multiple external devices, such IMDs communicate with only one external device at any given time. Moreover, the use of single communication channels in this manner is not an efficient allocation of available bandwidth.

Accordingly, it is desirable to have an IMD system that supports simultaneous multichannel data communication. In addition, it is desirable to have an IMD system that supports full duplex data communication. Furthermore, other desirable features and characteristics of the present invention will become apparent from the subsequent detailed description and the appended claims, taken in conjunction with the accompanying drawings and the foregoing technical field and background.

BRIEF SUMMARY

An IMD as described herein supports multichannel data communication with a plurality of "body area network" devices that are implanted in a patient's body, attached to the patient's body, carried by the patient, worn by the patient, or located in near proximity to the patient. The multichannel data communication techniques described herein support simultaneous full and/or half duplex communication with multiple body network devices.

The above and other aspects of the invention may be carried out in one form by an IMD configured for operation within the body of a patient, and configured for operation with at least one medical device within a body area network corresponding to the patient. The IMD includes, a communication module configured to support telemetry communication with at least one medical device. Further, the module includes a telemetry antenna arrangement coupled to the communication module, the telemetry antenna arrangement being configured to support telemetry communication with at least one medical device. Furthermore, the communication module and the telemetry antenna arrangement are configured to establish and maintain simultaneous multichannel telemetry communication with the at least one medical device.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
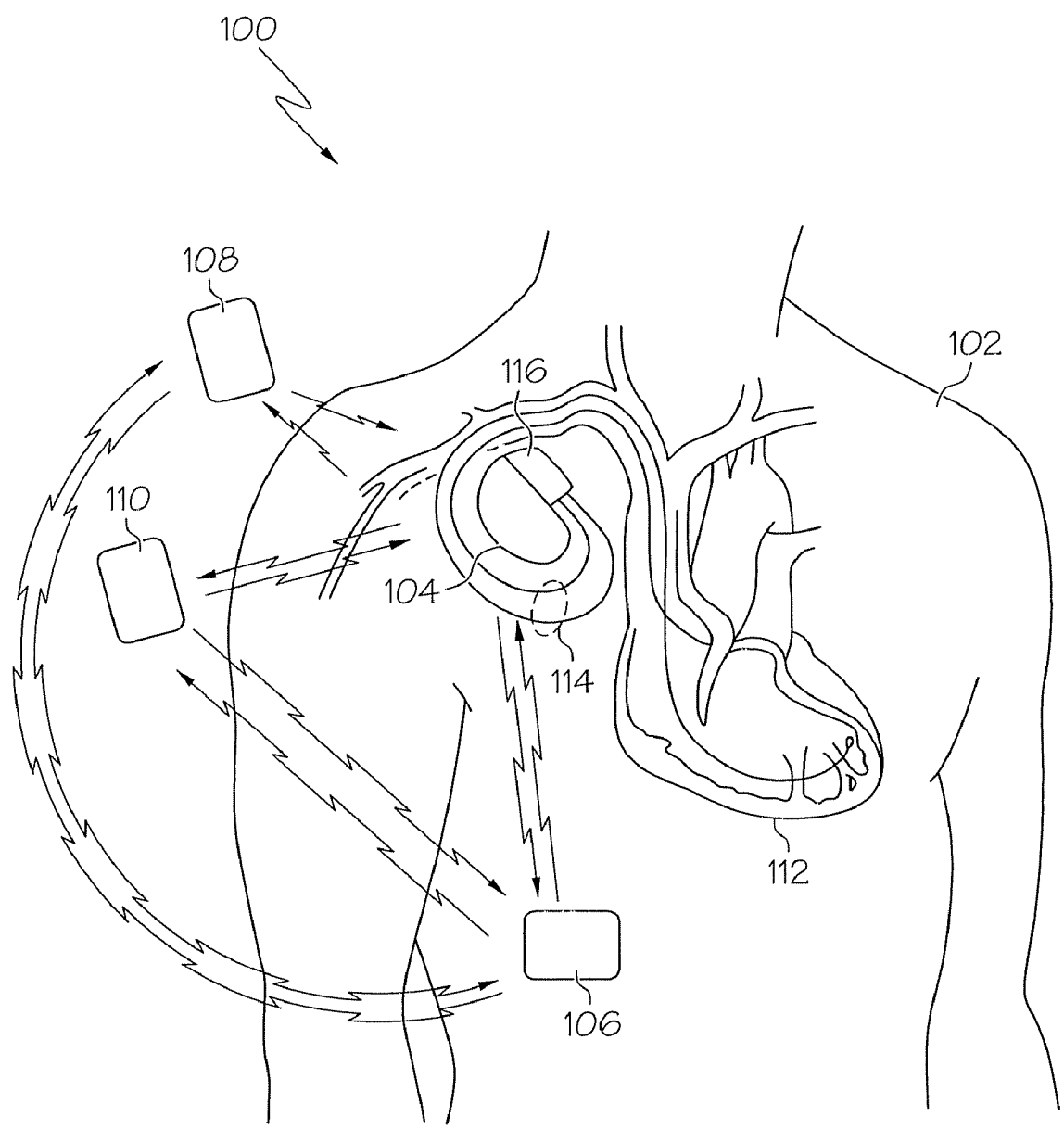
FIG. 1 is an illustration of a system including an IMD in accordance with certain embodiments of the invention.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the system described herein is merely one exemplary application for the invention.

For the sake of brevity, conventional techniques and features related to IMDs, IMD telemetry, signal processing, data transmission, signaling, network control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description refers to elements or features being "connected" or "coupled" together. As used herein, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although the figures may depict example arrangements of elements, additional intervening elements, devices, features, or components may be present in an actual embodiment (assuming that the functionality of the device/system is not adversely affected).

The embodiments of the present invention can be implemented with any IMD having wireless telemetry capabilities. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., artificial hearts). In addition, as the technology advances, it is contemplated that IMDs shall become even more complex with respect to programmable operating modes, menus of operating parameters, and monitoring capabilities of increasing varieties of physiologic conditions and electrical signals. It is to be appreciated that embodiments of the present invention will be applicable in such emerging IMD technology as well. Further, the embodiments of the invention can be implemented in more than one IMD implanted within the same patient to enable telemetry communication between the IMDs.

FIG. 1 illustrates bi-directional telemetry communication involving one or more IMDs in accordance with certain embodiments of the invention. FIG. 1 generally represents a body area network system 100 having multiple devices configured to communicate with one another. As used herein, a "body area network" is a localized network of communicating devices associated with a single patient 102, where devices within the body area network are suitably configured to communicate with each other using one or more data communication protocols. A body area network device may be an IMD, a device affixed to the patient (such as a physiologic characteristic sensor or monitor), a device worn or held by the patient (such as a remote control device for an IMD, a wireless monitor device for an IMD, or a handheld programmer for an IMD), or a device in close proximity to the patient (such as an external programmer that communicates with an IMD). In this example, system 100 generally includes an IMD 104 implanted within patient 102, another IMD 106 implanted within patient 102, and two external communication devices 108/110 that are not implanted within patient 102.

In certain embodiments, concurrent and multiple telemetry communications can take place between IMD 104 and any number of the devices within system 100. Moreover, telemetry communications may take place between devices (other than IMD 104) within system 100. The arrows in FIG. 1 represent such telemetry communications. In practice, a given communication session between two devices in system 100 may be unidirectional or bidirectional (in this example, FIG. 1 depicts bidirectional communications). In certain embodiments, the electrical devices can include one or more of at least one implantable medical instrumentation and of at least one external communication device. As shown in FIG. 1, in certain embodiments, the at least one implantable medical instrumentation can include IMD 104 and IMD 106, and the at least one external communication device can include external communication devices 108 and 110; however, it is to be appreciated that such quantities are not provided to limit the scope of application of embodiments of the invention.

In certain embodiments, when IMD 104 is used for cardiac applications (e.g., to provide cardiac sensing and pacing functions for patient 102), IMD 104 can be a cardiac device; for example, a pacemaker, an ICD, a hemodynamic monitor, or the like. As described above, however, neither IMD 104 nor any of the devices within system 100 should be limited to such applications or such devices. In this example, IMDs 104/106 are implanted in the same patient 102 beneath the patient's skin or muscle and, in certain embodiments, IMDs 104/106 can be typically oriented to the skin surface. In certain embodiments, when IMD 104 is used for cardiac applications, as shown, IMD 104 is electrically coupled to the heart 112 of the patient 102 through pace/sense or cardioversion/defibrillation electrodes operatively coupled to lead conductor(s) of one or more endocardial leads 114, which in turn, are coupled to a connector block 116 of IMD 104 in a manner well known in the art.

As generally mentioned above, among other design functions, each of the external communication devices 108/110 is designed for non-invasive communication with one or more of the IMDs 104/106, where such communication is enabled via transmit and receive communication channels, which will be further described below. In certain embodiments, one or more of the external communication devices 108/110 can be an external pressure reference monitor ("EPR"). An EPR is typically used to derive reference pressure data for use in combination with absolute pressure derived from an IMD. In addition, an EPR measures and records barometric pressure which is necessary for correlation to atmospheric pressure. However, it is to be appreciated that embodiments of the invention are not limited to such EPR applications. Generally, any form of portable programmer, interrogator, recorder, monitor, or telemetered signals transmitter and/or receiver found suitable for communicating with IMD 104 and/or IMD 106, in turn, could be used for external communication devices 108/110.

Figure 2:
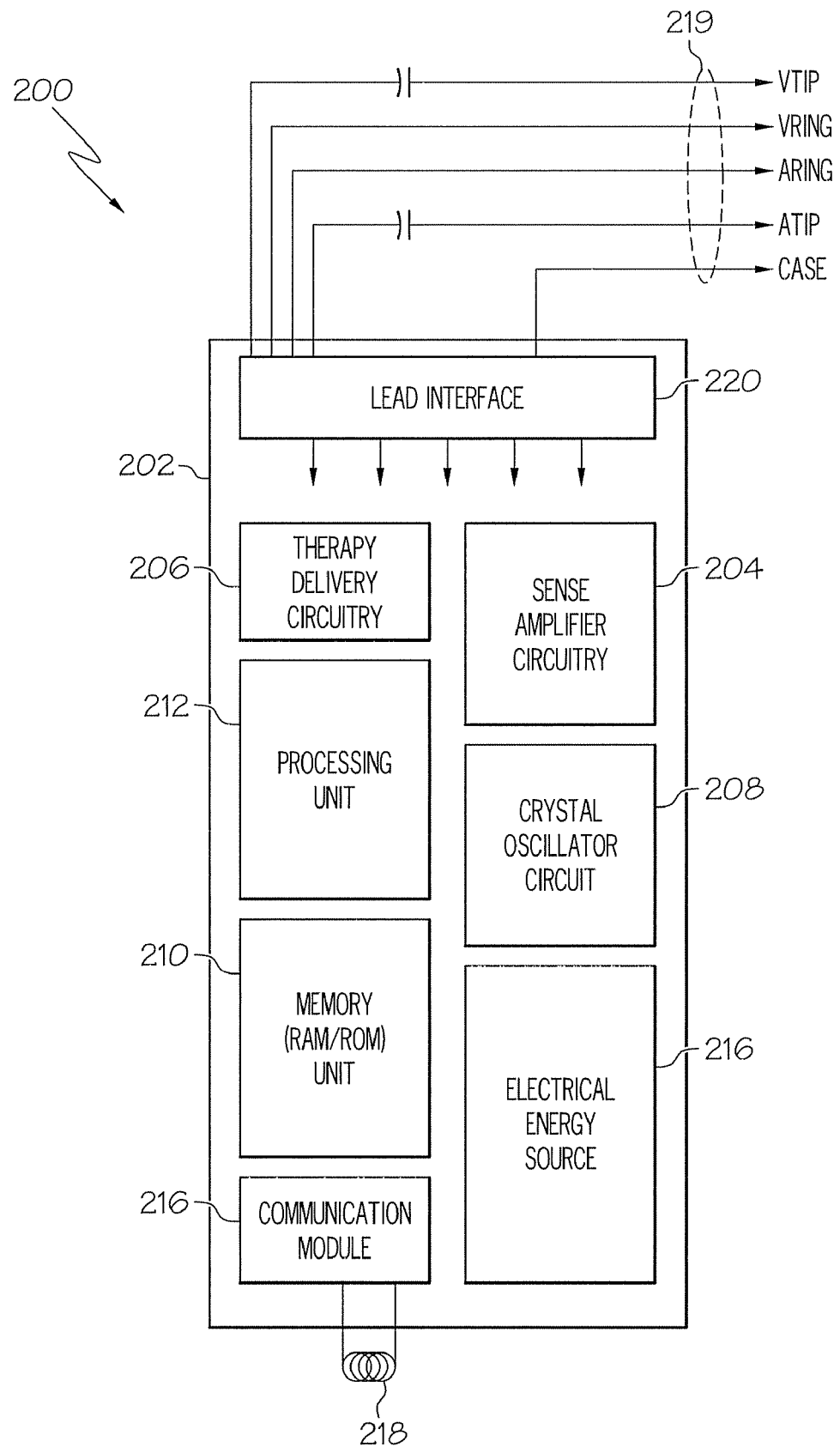
FIG. 2 is a block diagram of example circuitry of an IMD suitable for use in the system depicted in FIG. 1.

FIG. 2 shows an exemplary block diagram of the electronic circuitry of an IMD 200 configured in accordance with certain embodiments of the invention. IMD 104, IMD 106, and/or any other IMD implanted in patient 102 may be configured as shown in FIG. 2. As can be seen from FIG. 2, IMD 200 includes primary circuitry 202 for managing the operation and function of IMD 200, with such primary circuitry 202 being contained within a hermetic enclosure of IMD 200. The primary circuitry 202 includes a number of electrical components, most of which are exemplified in published United States patent application number 2002/0026224, entitled "Implantable Medical Device Incorporating Integrated Circuit Notch Filters" (incorporated herein by reference in relevant part). In certain embodiments, the primary circuitry 202 in FIG. 2 includes, without limitation, sense amplifier circuitry 204; therapy delivery circuitry 206; a crystal oscillator circuit 208; a suitable amount of memory 210, which may include random-access memory (RAM) and/or read-only memory (ROM); one or more processing units 212; and an electrical energy source 214. In certain embodiments, the primary circuitry 202 also includes a communication module 216 and one or more antennas 219 configured to enable IMD 200 to communicate with other devices within the body area network, e.g., any number of additional IMDs implanted within the same patient and/or any number of external devices. As described in more detail below, communication module 216 is suitably configured to support simultaneous multichannel communication between IMD 200 and a plurality of body area network devices. Moreover, communication module 216 is preferably configured to support full duplex communication between IMD 200 and one or more other devices within the body area network. It should be appreciated that the below descriptions of the primary circuitry 202 within the IMD 200 are merely example configurations.

In certain embodiments, when IMD 200 is used for cardiac applications (e.g., to provide cardiac sensing and pacing functions for the patient), the IMD 200 is coupled to the one or more endocardial leads 219 which, when implanted, extend transvenously between the implant site of the IMD 200 and the patient's heart, as previously noted with reference to FIG. 1. As mentioned above, the physical connections between the leads 219 and the various internal components of IMD 200 are facilitated by means of a conventional connector block assembly. Electrically, the coupling of the conductors of the leads 219 and internal electrical components of IMD 200 may be facilitated by means of a lead interface circuit 220 which functions, in a multiplexer-like manner, to selectively and dynamically establish necessary connections between various conductors in the leads 219 and individual electrical components of the IMD 200, as would be familiar to those of ordinary skill in the art. In certain embodiments, with respect to such cardiac applications, the various conductors in the leads 219 can include atrial tip and ring electrode conductors, $A_{TIP}$ and $A_{RING}$, and ventricular tip and ring electrode conductors, $V_{TIP}$ and $V_{RING}$. For the sake of clarity, the specific connections between the leads 219 and the various components of the IMD 200 are not shown in FIG. 2, although such connections will be familiar to those of ordinary skill in the art. For example, in cardiac applications, the leads 219 will necessarily be coupled, either directly or indirectly, to the sense amplifier circuitry 204 and the therapy delivery circuitry 206, in accordance with common practice, such that cardiac electrical signals may be conveyed to the sense amplifier circuitry 204 and such that stimulating pulses may be delivered by the therapy delivery circuitry 206 to cardiac tissue, via the leads 219. Also not shown in FIG. 2 is the protection circuitry commonly included in implanted devices to protect, for example, the sensing circuitry of the device from high voltage stimulating pulses.

As previously noted, the primary circuitry 202 includes one or more processing units 212 which generally varies in sophistication and complexity depending upon the type and functional features of the IMD 200. In certain embodiments, the processing unit 212 can be an off-the-shelf programmable microprocessor, a microcontroller, a custom integrated circuit, or any of a wide variety of other implementations generally known. Although specific connections between the processing unit 212 and other components of the IMD 200 are not shown in FIG. 2, it will be apparent to those of ordinary skill in the art that the processing unit 212 functions to control the timed operation of the sense amplifier circuitry 204 and the therapy delivery circuitry 206. In certain embodiments, the functioning of the processing unit 212 would be under control of firmware and programmed software algorithms stored in memory 210 (e.g., RAM, ROM, PROM and/or reprogrammable ROM) and are carried out using a processing unit of a typical microprocessor core architecture. In certain embodiments, the processing unit 212 may also include multiple processors with a watchdog circuit, a DMA controller, a lock mover/reader, a CRC calculator, and other specific logic circuitry coupled together by on-chip bus, address bus, power, clock, and control signal lines in paths or trees in a manner well known in the art.

In certain embodiments, as is known in the art, the electrical energy source 214 powers the primary circuitry 202 and can also be used to power electromechanical devices, such as valves or pumps, of a substance delivery IMD, or to provide electrical stimulation energy of an ICD shock generator, cardiac pacing pulse generator, or other electrical stimulation generator. In certain embodiments, the electrical energy source 214 is a high energy density, low voltage battery coupled with a power supply circuit having power-on-reset ("POR") capability. The power supply circuit provides one or more low voltage power supply signals, the POR signal, one or more voltage reference sources, current sources, an elective replacement indicator ("ERI") signal, and, in the case of an ICD, high voltage power to the therapy delivery circuitry 206. For the sake of clarity in the example block diagram provided in FIG. 2, the connections between the electrical energy source 214 and the electrical components of the IMD 200 are not shown, as one skilled in the art would be familiar with such connections.

In certain embodiments, the sense amplifier circuitry 204 can be configured to process physiologic signals that are used to trigger or modulate therapy delivery and are stored as physiologic signal data for later retrieval as described herein. Generally, the sense amplifier circuitry 204 is coupled to electrical signal sense electrodes and/or physiologic sensors on or in the housing of the IMD 200 or as mentioned above, situated at sites distanced from the IMD housing, typically in distal portions of the elongated leads 219. As is generally known, the sensors or electrodes located outside the housing are coupled by conductors to feedthrough pins of feedthroughs extending through the housing wall. Certain physiologic sensors or sense electrodes can be mounted to a connector assembly so that the conductors are quite short.

In certain embodiments, the conductors include the elongated conductors of the leads 219 extending to the remotely situated physiologic sensors and sense electrodes. As such, in some cardiac applications, the sense amplifier circuitry 204 is designed to receive electrical cardiac signals from the leads 219 and to process such signals to derive event signals reflecting the occurrence of specific cardiac electrical events, including atrial contractions (P-waves) and ventricular contractions (R-waves). These event-indicating signals are provided to the processing unit 212 for use in controlling the synchronous stimulating operations of the IMD 200 in accordance with common practice in the art. In addition, these event indicating signals may be communicated, via uplink transmission, to one or more external communication devices.

In example embodiments, the therapy delivery circuitry 206 can be configured to deliver electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart. Alternatively, in certain embodiments, the therapy delivery circuitry 206 can be configured as a drug pump delivering drugs into organs for therapeutic treatment or into the spinal column for pain relief. Alternatively, in certain embodiments, the therapy delivery circuitry 206 can be configured to operate an implantable heart assist device or pump implanted in patients awaiting a heart transplant operation.

When the IMD 200 is used for cardiac applications, the sense amplifier circuitry 204 may also include patient activity sensors or other physiologic sensors for sensing the need for cardiac output and modulating pacing parameters accordingly through many alternative approaches set forth in the prior art. If the IMD 200 is an ICD, the therapy delivery circuitry 206 generally includes one or more high power cardioversion/defibrillation output capacitors, electronic circuitry coupled to the sense amplifiers for detecting and discriminating pathologic and/or nonpathologic arrhythmias from one another and providing other functions, high voltage electronic circuitry for charging the output capacitor(s) from a battery voltage to a higher voltage, and electronic switching circuitry for dumping the charge built up on the output capacitor(s) through the cardioversion/defibrillation electrodes operatively coupled to the one or more endocardial leads 219.

Such IMDs are described in detail in U.S. Pat. Nos. 5,626,620 and 5,931,857 (which are incorporated herein by reference in their relevant parts).

Registers of the memory 210 can be used for storing data compiled from sensed cardiac activity and/or relating to device operating history or sensed physiologic parameters. Generally, the data storage can be triggered manually by the patient, on a periodic basis, or by detection logic (e.g., within the sense amplifier circuitry 204) upon satisfaction of certain programmed-in event detection criteria. If not manually triggered, in certain embodiments, the criteria for triggering data storage within the IMD 200 is programmed via telemetry transmitted instructions and parameter values. If manually triggered, in some cases, the IMD 200 could include a magnetic field sensitive switch that closes in response to a magnetic field, and the closure causes a magnetic switch circuit to issue a switch closed ("SC") signal to the processing unit 212 which responds in a "magnet mode." For example, the patient may be provided with a magnet (e.g., incorporated into an external communication device) that can be applied over the IMD 200 to close the switch and prompt the processing unit 212 to store physiologic episode data when the patient experiences certain symptoms and/or deliver a therapy to the patient. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

In certain embodiments, the crystal oscillator circuit 208 generally employs clocked CMOS digital logic ICs having a clock signal provided by a crystal (e.g., piezoelectric) and a system clock coupled thereto as well as discrete components, e.g., inductors, capacitors, transformers, high voltage protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 200 (e.g., processing unit 212) are omitted from FIG. 2 for the sake of clarity.

Those of ordinary skill in the art will appreciate that IMD 200 may include numerous other components and subsystems, for example, activity sensors and associated circuitry. The presence or absence of such additional components in IMD 200, however, is not believed to be pertinent to the present invention, which relates to the implementation and operation of a communication subsystem in the IMD 200, and associated communication subsystems in one or more of further implantable medical instrumentation and other electrical devices, such as external communication devices.

In certain embodiments, the IMD 200 can involve an implantable cardiac monitor without therapy delivery system 206, e.g., an implantable EGM monitor for recording the cardiac electrogram from electrodes remote from the heart as disclosed in U.S. Pat. No. 5,331,966 (which is incorporated by reference herein in its relevant part). Alternatively, the IMD 200 can involve an implantable hemodynamic monitor ("IHM") for recording cardiac electrogram and other physiologic sensor derived signals, e.g., one or more of blood pressure, blood gases, temperature, electrical impedance of the heart and/or chest, and patient activity. The MEDRONIC® REVEAL® insertable loop recorder, having EGM electrodes spaced across its housing, is an example of the former, and the MEDRONIC® CHRONICLE® IHM, coupled with a capacitive pressure and temperature sensing lead and EGM sense electrodes of the type described in U.S. Pat. No. 5,564,434 (which is incorporated herein by reference in its relevant part) is an example of the latter.

As described above, the IMD 200 includes communication module 216 and one or more antennas 218. In certain embodiments, each of the antennas 218 is mounted to the IMD 200 in one or more of a wide variety of configurations. For example, one or more of the antennas 218 can take the form of a surface mounted antenna (e.g., as described in U.S. Pat. No. 4,401, 119, which is incorporated herein by reference in its relevant part), or one or more of the antennas 218 can be enclosed within or mounted to the IMD connector block assembly. However, it is to be appreciated that the invention should not be limited to such.

It is desirable to reduce the size of the IMD 200 while increasing its functional capabilities and prolonging battery life to increase longevity. In accordance with certain embodiments, the current consumption of certain transceiver circuits can also be decreased to accomplish that goal. By way of background, the IMD telemetry system and functions are described as follows. For convenience of description, the embodiments described as follows use short range RF downlink telemetry transmissions and uplink telemetry transmissions, but it should be appreciated that the embodiments of the invention should not be limited to such. Similarly, the terms "telemeter," "telemetry transmission," and the like are intended to embrace any such action and manner of communicating and conveying data and commands between the IMD 200 and other electrical devices within the body area network (e.g., other IMDs implanted within the same patient, external communication devices carried or worn by the patient, and/or external monitoring devices) in the uplink transmission direction and the downlink transmission direction.

In the IMD 200, uplink and downlink telemetry capabilities are provided to enable concurrent communication with multiple devices within the body area network. IMD 200 may also be configured to communicate in a conventional manner with one or more external electrical devices, a more proximal medical device on the patient's body, or other implantable medical instrumentation in the patient's body. Generally, the stored physiologic data as well as one or more of real-time generated physiologic data and non-physiologic data (collectively referred to herein as "patient data") can be transmitted by uplink RF telemetry from the IMD 200 to the other devices or instrumentation in response to a downlink telemetered interrogation command, events within the IMD 200 or the patient, magnet swipe across the IMD 200 by the patient, upon satisfaction of certain programmed-in event detection criteria and/or timed events. The real-time physiologic data can include real time sampled signal levels, e.g., intracardiac electrocardiogram amplitude values, and sensor output signals. The non-physiologic patient data can include currently programmed device operating modes and parameter values, battery condition, device ID, patient ID, implantation dates, device programming history, real time event markers, and the like. In the context of implantable pacemakers and ICDs, such patient data can include programmed sense amplifier sensitivity, pacing or cardioversion pulse amplitude, energy, and pulse width, pacing or cardioversion lead impedance, programmed setting, and/or accumulated statistics related to device performance, e.g., data related to detected arrhythmia episodes and applied therapies.

Figure 3:
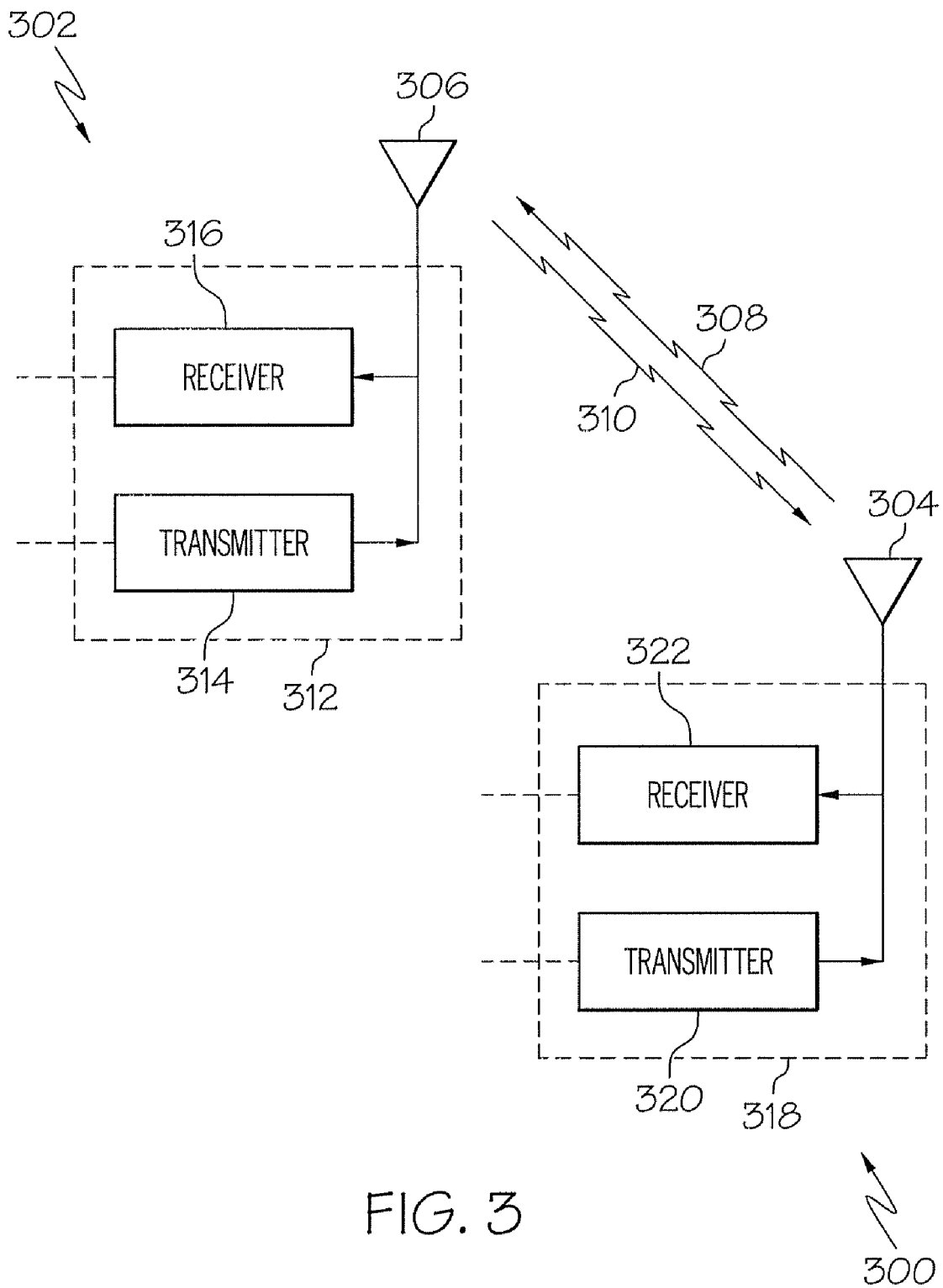
FIG. 3 is a block diagram depicting example communication modules suitable for use in an IMD communication system.

FIG. 3 depicts data communication between an IMD 300 and another device 302 within a body area network. In certain embodiments, programming commands or patient data can be transmitted between one or more IMD antennas 304 associated with the IMD 300 and one or more antennas 306 associated with the device 302. In certain embodiments, a high frequency signal can be employed. As such, it would not be necessary for antenna 306 to be held in close proximity to IMD 300. In other words, the system shown in FIG. 3 may be configured to support far field telemetry. For example, an external communication device 302 and an external communication device antenna 306 may be on a stand a few meters or so away from the patient. Moreover, the patient may be active and could be exercising on a treadmill or the like during a telemetry interrogation and transmission of real time ECG or physiologic parameters. An external communication device 302 may also be designed to universally program existing IMDs that employ the conventional ferrite core, wire coil, RF telemetry antenna of the prior art and therefore also have a conventional external communication device RF head and associated software for selective use with such IMDs.

In an uplink telemetry transmission 308, the antenna 306 operates as a telemetry receiver antenna, and the antenna 304 operates as a telemetry transmitter antenna. Conversely, in a downlink telemetry transmission 310, the antenna 306 operates as a telemetry transmitter antenna, and the antenna 304 operates as a telemetry receiver antenna. As shown with respect to FIG. 1, such telemetry transmissions may also be supported between two IMDs implanted within the same patient. As such, it is to be appreciated that IMDs and external communication devices within a body area network can be similarly configured as described herein to facilitate multi-channel telemetry communications.

In certain embodiments, antenna 306 is electrically coupled to a telemetry transceiver or radio 312, which may include a telemetry transmitter 314 and telemetry receiver 316. Similarly, in certain embodiments, antenna 304 is coupled to a telemetry transceiver or radio 318, which may include a telemetry transmitter 320 and telemetry receiver 322. Referring to FIG. 2, telemetry transceiver 318 may be included within communications module 216 of the IMD 200. Alternatively, telemetry transceiver 318 may be coupled to communications module 216 to enable IMD operation as described herein. In certain embodiments, the telemetry transmitter and telemetry receiver of a given device can be coupled to control circuitry and registers under the control of a microcomputer and software maintained by the device.

In practice, the telemetered data can be encoded in any of a wide variety of telemetry formats. While not being limited to such, some examples of particular data encoding or modulation types and/or techniques that can be utilized with such data transmissions include noise modulation, general spread spectrum encoding, bi-phase encoding, frequency shift keying ("FSK"), time division multiple access ("TDMA"), frequency division multiple access ("FDMA"), pre-emphasis/de-emphasis of baseband, vestigial, code division multiple access ("CDMA"), quadrature amplitude modulation ("QAM"), pi/8, quad-QAM, 256-QAM, 16-QAM, delta modulation, phase shift keying ("PSK"), quadrature phase shift keying ("QPSK"), quadrature amplitude shift keying ("QASK"), minimum shift keying, tamed frequency modulation ("TFM"), orthogonal frequency division multiplexing ("OFDM"), Bluetooth, any 802.11 modulation configuration, worldwide interoperability for microwave access ("WiMAX"), any 802.16 modulation configuration, 802.15.4, and Zigbee.

In certain embodiments, the uplink and downlink telemetry transmissions 308/310 between the IMD 300 and the device 302 follow a telemetry protocol that formulates, transmits, and demodulates data packets each comprising a bit stream of modulated data bits. In certain embodiments, the data packets are formulated of a data bit stream with a preamble, data and error checking data bits.

Figure 4:
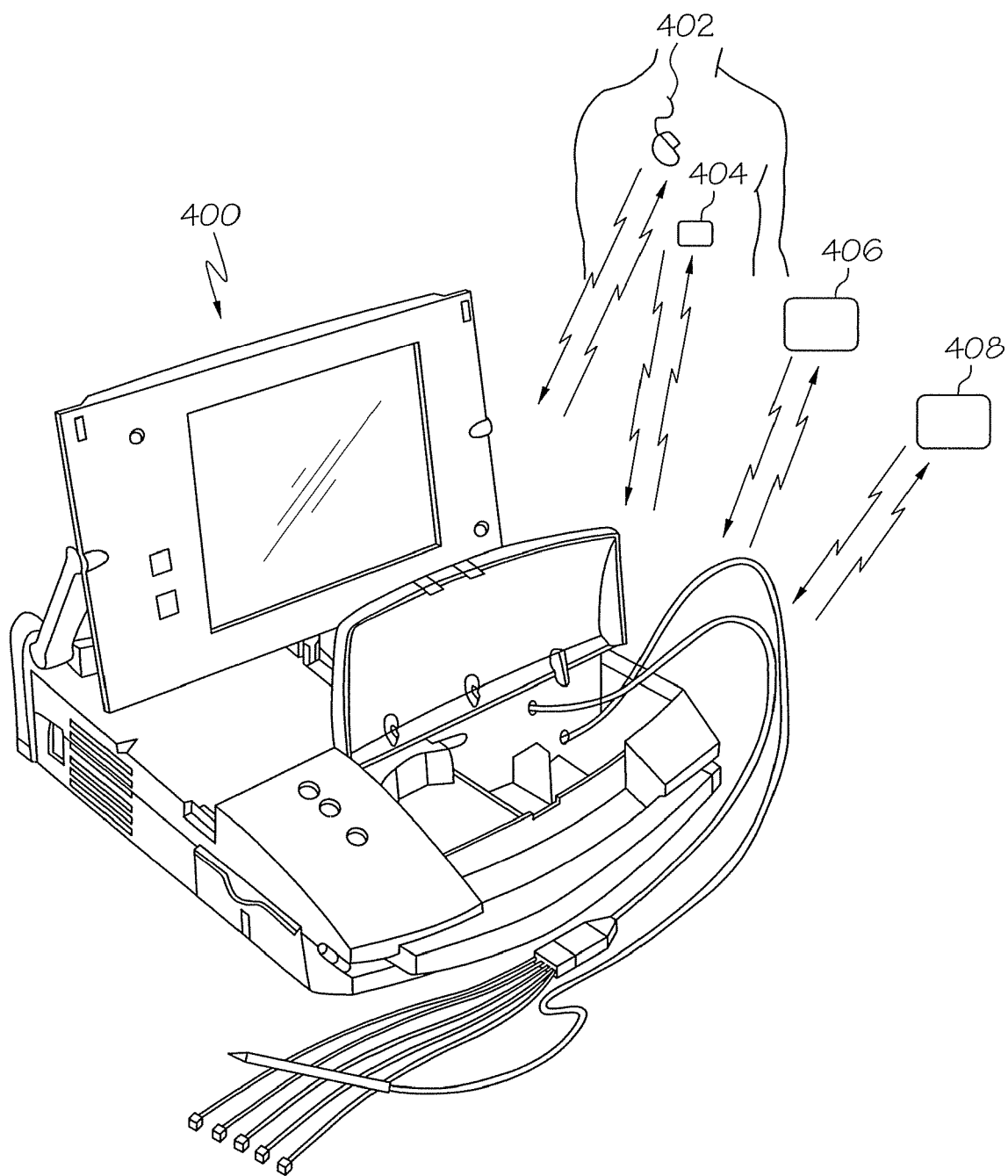
FIG. 4 is a perspective view of an external processing monitor configured in accordance with certain embodiments of the invention.

In FIG. 4, there is shown a perspective view of an external processing monitor 400 configured in accordance with certain embodiments of the invention. In certain embodiments, the external processing monitor 400 can be used for simultaneous multichannel telemetry communication with any number of IMDs 402/404 and/or any number of external communication devices 406/408. From such telemetry communications, the external processing monitor 400 can be subsequently used to display or further transmit patient data. The external processing monitor 400 generally includes a processing unit (not visibly shown). As should be appreciated, the processing unit can include any of a wide variety of devices. While not being limited to such, the processing unit, in certain embodiments, can be a personal computer type motherboard, e.g., a computer motherboard including one or more microprocessors and related circuitry such as digital memory. The details of design and operation of the computer system will not be set forth in detail in the present disclosure, as it is believed that such details are well-known to those of ordinary skill in the art. However, such external processing monitors are described in more detail in U.S. Pat. Nos. 5,345,362 and 5,683,432, which are incorporated herein by reference in their relevant parts. While not shown, it is to be appreciated that such telemetry communications between the external processing monitor 400 and the devices within the body area network (e.g., IMDs 402/404 and external communication devices 406/408) can occur in combination with telemetry communications occurring between IMDs 402/404, between external communication devices 406/408, and/or between one or more of the IMDs 402/404 and one or more of the external communication devices 406/408 (as exemplified in FIG. 1).

Figure 5:
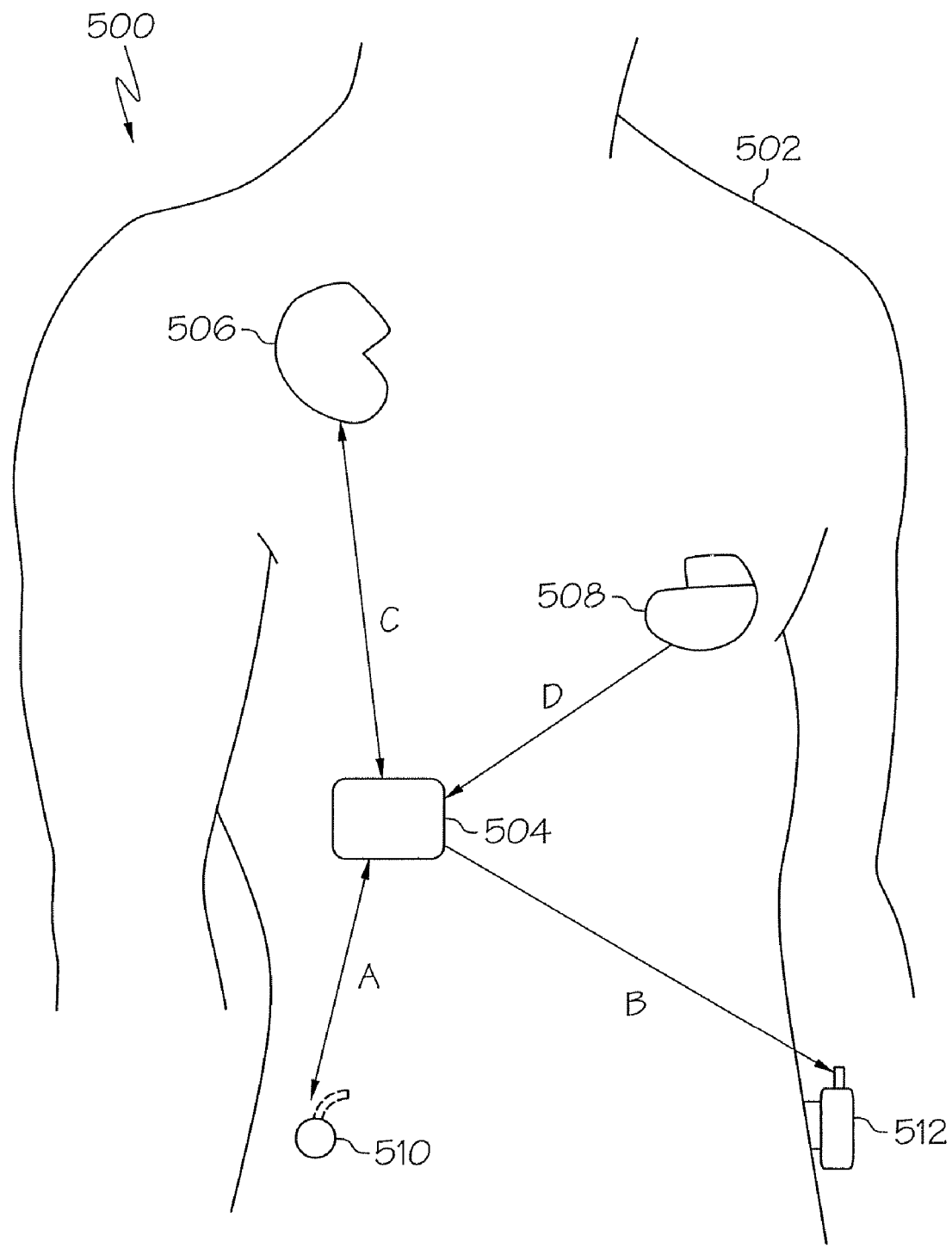
FIG. 5 is a diagram of a body area network having an IMD that supports simultaneous multichannel communication.

FIG. 5 is a diagram of a body area network 500 having at least one IMD that supports simultaneous multichannel communication. Body area network 500 includes a number of devices for a patient 502, where such devices are either implanted within the body of the patient 502, worn by the patient 502, attached or coupled to the body of the patient 502, carried by the patient 502 or are otherwise located within close proximity of the patient. Thus, a practical body area network may include any number of IMDs and/or any number of non-implanted devices. Each of the devices in body area network 500 is suitably configured to communicate with at least one other device in body area network 500. This example body area network 500 includes an IMD 504, an IMD 506, an IMD 508, a transdermal physiologic characteristic sensor 510, and an external device 512 that is worn by patient 502 during normal operation. Other example embodiments may utilize more or less devices, and different types of devices, than that shown in FIG. 5.

Although any of the devices in body area network 500 may be configured to support multichannel communication as described herein, FIG. 5 only depicts IMD 504 in a multichannel communication mode. Generally, IMD 504 is configured for operation within the body of patient 502 as described in more detail above. Moreover, IMD 504 is configured to communicate with at least one additional medical device within body area network 500, and, in this example, with at least one additional IMD 506/508 located within the body of the patient 502. For example, FIG. 5 depicts IMD 504 and sensor 510 communicating via a bidirectional data communication channel (Channel A), IMD 504 communicating with external device 512 via a unidirectional data communication channel (Channel B), IMD 504 and IMD 506 communicating via a bidirectional data communication channel (Channel C), and IMD 508 communicating with IMD 504 via a unidirectional data communication channel (Channel D). The communication channels depicted in FIG. 5 are intended to represent simultaneously maintained channels that operate in a concurrent manner to enable IMD 504 to support multichannel communication with one or more devices within body area network 500. A given communication channel may be unidirectional or bidirectional to suit the needs of the particular application, depending upon the capabilities of the devices within body area network 500, and/or depending upon other practical operating considerations.

Figure 6:
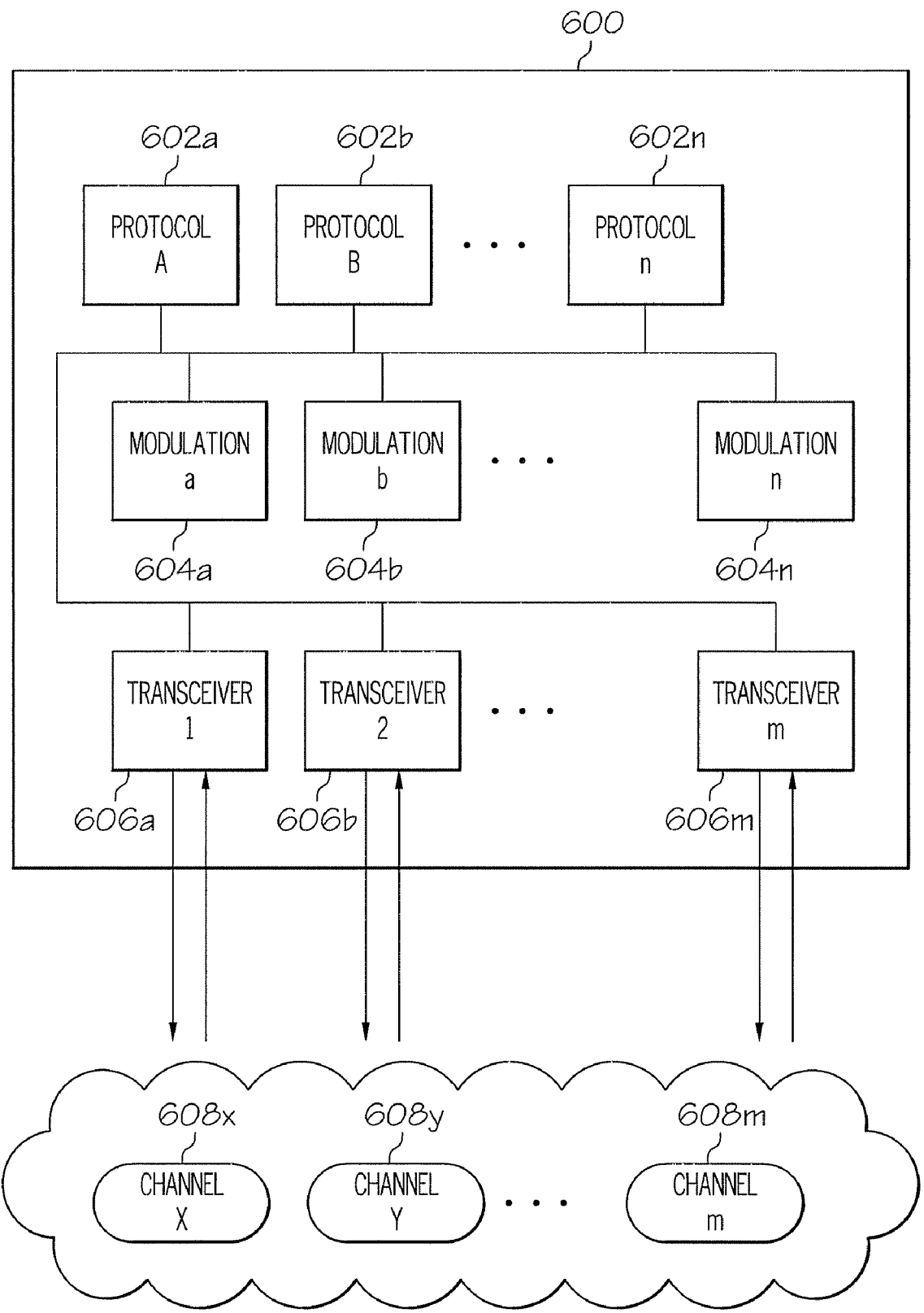
FIG. 6 is a schematic representation of an example multichannel communication module configured in accordance with an example embodiment of the invention.

FIG. 6 is a schematic representation of an example multichannel communication module 600 configured in accordance with an example embodiment of the invention. Module 600 may, for example, be implemented in IMD 504 or in any of the devices shown in FIG. 5. Communication module 600 is generally configured to support telemetry communication with at least one other medical device, e.g., IMDs or other devices within a body area network. In practice, communication module 600 can be coupled to a telemetry antenna arrangement having one or more telemetry antennas, where the telemetry antenna arrangement is suitably configured to support telemetry communication with at least one other medical device. Example telemetry antenna arrangements were described above in connection with FIGS. 1-4.

Depending upon the particular implementation, communication module 600 may be configured to establish and maintain the simultaneous multichannel telemetry communication with other devices using different data communication protocols and/or different modulation schemes. Accordingly, FIG. 6 depicts a generalized and flexible configuration where communication module 600 is capable of supporting telemetry communication using data communication protocols A, B, and so on, up to an arbitrary number (N) of different protocols 602. Likewise, FIG. 6 depicts a generalized and flexible configuration where communication module 600 is capable of supporting telemetry communication using modulation schemes a, b, and so on, up to an arbitrary number (n) of different modulation schemes 604. The variables N and n need not be correlated in any way.

Communication module 600 may include (or communicate with) processing logic that enables the selection of an appropriate data communication protocol 602 and/or modulation scheme 604 for a particular communication channel. For this reason, FIG. 6 schematically depicts the various protocols 602 and modulation schemes 604 as functional blocks that are interconnected. Example embodiments may utilize one or more of the data communication protocols and/or one or more of the modulation schemes described above in connection with FIG. 3. Some of the modulation schemes could include, without limitation: FSK, DPSK, DQPSK, DPSK, and others. Some of the communication protocols could include, without limitation: Zigbee, Bluetooth, IEEE 802.11, or the like.

Although not a requirement of the invention, communication module 600 may utilize multiple transceivers 606 configured to support the multichannel communication techniques described herein. FIG. 6 depicts a generalized and flexible configuration where communication module 600 includes an arbitrary number (M) of different transceivers. In this regard, a practical communication module 600 may utilize a single configurable transceiver 606 that can support a plurality of simultaneous communication channels. Alternatively, a practical communication module 600 may utilize multiple transceivers 606 as necessary to support the different channels, different modulation schemes, or the like. Moreover, each individual transceiver 606 may include one or more associated telemetry antennas that may be suitably configured in accordance with the particular transceiver characteristics. FIG. 6 depicts each transceiver 606 supporting a bidirectional data communication channel, however, embodiments of the invention are not so limited, and a given transceiver 606 may be suitably configured to support a unidirectional data communication channel (incoming or outgoing).

FIG. 6 also depicts communication module 600 maintaining an arbitrary number (m) of independent data communication channels 608. Notably, the variables M and m need not be correlated in any way. These communication channels 608 represent simultaneous channels that are concurrently supported by the device in which communication module 600 resides. Communication module 600, along with its associated telemetry antenna arrangement, may be designed to establish and maintain a first telemetry communication channel with at least one device in the body area network using a first data communication protocol 602, and to establish and simultaneously maintain a second telemetry communication channel with at least one device in the body area network using a different data communication protocol 602. Similarly, communication module 600, along with its associated telemetry antenna arrangement, may be designed to establish and maintain a first telemetry communication channel with at least one device in the body area network using a first modulation scheme 604, and to establish and simultaneously maintain a second telemetry communication channel with at least one device in the body area network using a different modulation scheme 604. In either situation, the different channels may be maintained between communication module 600 and one other device, or between communication module 600 and a plurality of other devices.

In specific embodiments, one or more of these communication channels 608 is a full-duplex channel that accommodates simultaneous data transmission and reception by the device. Indeed, communication module 600 and the respective telemetry antenna arrangement can be suitably configured to establish and maintain simultaneous full-duplex multichannel telemetry communication with one or more devices within a body area network. In one example embodiment, communication module 600 and its associated telemetry antenna arrangement are suitably configured to establish and maintain the multiple channels using a single carrier frequency. In practice, the carrier frequency may be between 401 MHz and 406 MHz, which is a frequency band that is commonly utilized for IMD applications.

Figure 7:
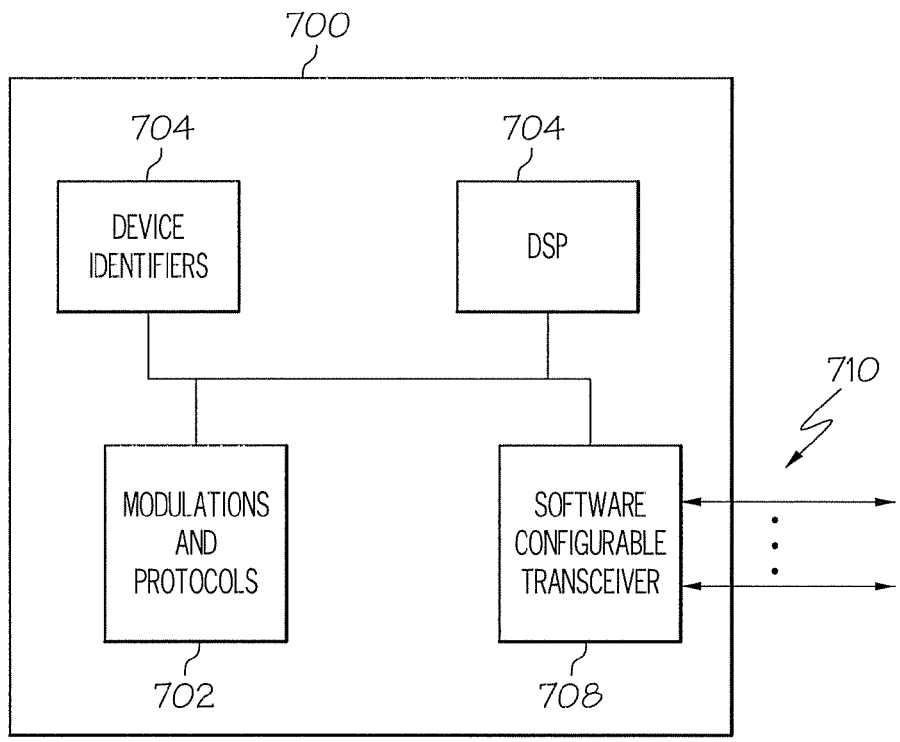
FIG. 7 is a schematic representation of an example IMD that supports multichannel communication.

FIG. 7 is a schematic representation of an example IMD 700 that supports multichannel communication. It should be appreciated that an embodiment of IMD 700 will include additional components and logic that support conventional operating aspects of IMD 700. IMD 700 may include logic 702 associated with different supported modulation schemes and data communication protocols as described previously, logic or memory 704 associated with device identifiers, a processing unit such as a digital signal processor 706, and a software configurable transceiver 708 configured to support simultaneous multichannel communication with one or more devices within a body area network.

IMD 700 may store device identifiers 704 corresponding to the other devices within the body area network and/or corresponding to any devices with which IMD 700 can communicate. These device identifiers 704 may be linked to respective modulation schemes and/or communication protocols 702 such that IMD 700 can select an appropriate communication protocol and an appropriate modulation scheme for data communication with the identified devices. In this example, DSP 706 is configured to control and manage the configuration of transceiver 708 such that IMD 700 can maintain a plurality of concurrent communication channels 710. Transceiver 708 is software configurable in the sense that it's operating parameters and characteristics can be modified by DSP 706 as needed, depending upon the selected modulation scheme and communication protocol.

Figure 8:
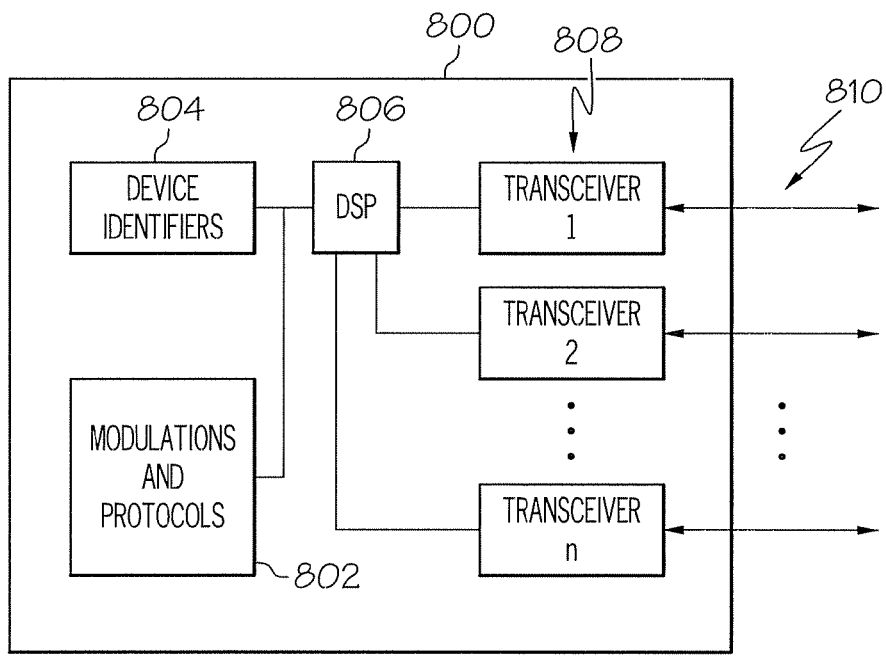
FIG. 8 is a schematic representation of another example IMD that supports multichannel communication.

FIG. 8 is a schematic representation of another example IMD 800 that supports multichannel communication. It should be appreciated that an embodiment of IMD 800 will include additional components and logic that support conventional operating aspects of IMD 800. IMD 800 may include logic 802 associated with different supported modulation schemes and data communication protocols as described previously, logic or memory 804 associated with device identifiers, a processing unit such as a digital signal processor 806, and a bank of transceivers or radios 808 configured to support simultaneous multichannel communication with one or more devices within a body area network.

IMD 800 generally operates as described above in connection with IMD 700. IMD 800, however, employs a plurality of transceivers 808 rather than a software configurable transceiver. Each of the transceivers 808 may be suitably configured for optimized support of one or more of the possible communication protocols and modulation schemes 802 supported by IMD 800. Moreover, IMD 800 may use a distinct transceiver 808 for each of the multiple data communication channels 810 it establishes and maintains.

In operation, an IMD (or other device within a body area network) as described herein may include intelligence and processing power that enables it to select a desired data communication protocol and a desired modulation scheme for each of the multiple telemetry communication channels. For example, the IMD may select the data communication protocol and/or modulation scheme for a first channel, and establish full-duplex communication with another device using the selected parameters. In addition, the IMD may select a data communication protocol (which may, but need not, be different) and/or modulation scheme (which may, but need not, be different) for a second channel, and establish full-duplex communication with another device using the selected parameters. Once the simultaneous multichannel communication has been established, the IMD can maintain the multiple channels as needed during the given time period.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

The invention claimed is:

1. An implantable medical device ("IMD") configured for operation within the body of a patient, and further configured for operation with a plurality of different medical devices within a body area network corresponding to the patient, the IMD comprising:
    a wireless communication module configured to support wireless telemetry communication with the plurality of different medical devices; and
    a wireless telemetry antenna arrangement coupled to the wireless communication module, the wireless telemetry antenna arrangement being configured to support wireless telemetry communication with the plurality of different medical devices; wherein
    the wireless communication module and the wireless telemetry antenna arrangement being configured to establish and maintain simultaneous wireless multichannel telemetry communication with the plurality of different medical devices.

2. An IMD according to claim 1, the wireless telemetry antenna arrangement comprising a plurality of wireless telemetry antennas.

3. An IMD according to claim 1, the wireless communication module and the wireless telemetry antenna arrangement being configured to establish and maintain simultaneous wireless multichannel telemetry communication with the at least one medical device using a single carrier frequency.

4. An IMD according to claim 3, wherein the single carrier frequency is between about 401 MHz and 406 MHz.

5. An IMD according to claim 1, the wireless communication module and the wireless telemetry antenna arrangement being configured to establish and maintain simultaneous full-duplex wireless multichannel telemetry communication with the at least one medical device.

6. An IMD according to claim 1, the wireless communication module comprising multiple transceivers.

7. An IMD according to claim 1, the wireless communication module and the wireless telemetry antenna arrangement being configured to establish and maintain simultaneous wireless multichannel telemetry communication with the at least one medical device using a frequency division multiple access protocol.

8. IMD according to claim 1, the wireless communication module and the wireless telemetry antenna arrangement being configured to establish and maintain simultaneous wireless multichannel bidirectional telemetry communication with the at least one medical device.

9. An IMD according to claim 1, the wireless communication module and the wireless telemetry antenna arrangement being configured to maintain a first wireless telemetry communication channel with the at least one medical device using a first wireless data communication protocol, and to simultaneously maintain a second wireless telemetry communication channel with the at least one medical device using a second wireless data communication protocol that is different than the first wireless data communication protocol.

10. An IMD according to claim 1, the wireless communication module and the wireless telemetry antenna arrangement being configured to maintain a first wireless telemetry communication channel with the at least one medical device using a first modulation scheme, and to maintain a second wireless telemetry communication channel with the at least one medical device using a second modulation scheme that is different than the first modulation scheme.

11. A medical device body area network for a patient, the body area network comprising:
    a plurality of medical devices located within close proximity of the patient; and
    an implantable medical device ("IMD") configured for operation within the body of the patient, and configured to wirelessly communicate with the plurality of medical devices, the IMD comprising:
    a wireless communication module configured to support wireless telemetry communication with the plurality of medical devices; and
    a wireless telemetry antenna arrangement coupled to the wireless communication module, the wireless telemetry antenna arrangement being configured to support wireless telemetry communication with the plurality of medical devices; wherein
    the wireless communication module and the wireless telemetry antenna arrangement being configured to establish and maintain simultaneous wireless multichannel telemetry communication with the plurality of medical devices; and
    the wireless communication module and the wireless telemetry antenna arrangement being configured to maintain a first wireless telemetry communication channel with one of the plurality of medical devices using a first wireless data communication protocol, and to simultaneously maintain a second wireless telemetry communication channel with another one of the plurality of medical devices using a second wireless data communication protocol that is different than the first wireless data communication protocol.

12. A medical device body area network according to claim 11, the plurality of medical devices comprising a second IMD configured for operation within the body of the patient.

13. A medical device body area network according to claim 11, the plurality of medical devices comprising a non-implanted device.

14. A medical device body area network according to claim 11, the wireless communication module and the wireless telemetry antenna arrangement being configured to establish and maintain simultaneous full-duplex wireless multichannel telemetry communication with the plurality of medical devices.

15. A medical device body area network according to claim 11, the wireless communication module and the wireless telemetry antenna arrangement being configured to maintain the first wireless telemetry communication channel with the at least one medical device using a first modulation scheme, and to maintain the second wireless telemetry communication channel with the at least one medical device using a second modulation scheme that is different than the first modulation scheme.

16. A data communication method for an implantable medical device ("IMD") configured for operation within the body of a patient, and configured for operation with a plurality of medical devices within a body area network corresponding to the patient, the method comprising:
    storing device identifiers corresponding to the plurality of medical devices, each of the device identifiers being linked to respective modulation schemes and wireless data communication protocols for the plurality of medical devices;
    selecting, based on the device identifiers corresponding to the plurality of medical devices, one of the respective modulation schemes and one of the wireless data communication protocols for each of a plurality of wireless telemetry communication channels associated with the plurality of medical devices, the selecting step resulting in selected modulation schemes and selected wireless data communication protocols;

establishing the plurality of wireless telemetry communication channels using the selected modulation schemes and the selected wireless data communication protocols; and maintaining simultaneous wireless multichannel telemetry communication with the plurality of medical devices using the plurality of wireless telemetry communication channels.

* * * * *